United States Patent [19]

Tedeschi

[11] Patent Number: 5,524,476
[45] Date of Patent: Jun. 11, 1996

[54] METHOD AND APPARATUS FOR INSURING THE INTEGRITY OF VEHICLE TESTING PROCEDURES

[75] Inventor: Rinaldo R. Tedeschi, Newington, Conn.

[73] Assignee: Environmental Systems Products, Inc., East Granby, Conn.

[21] Appl. No.: 512,384

[22] Filed: Aug. 8, 1995

[51] Int. Cl.⁶ .................................................. G01N 7/00
[52] U.S. Cl. .................................... 73/23.31; 194/202
[58] Field of Search .................... 194/202; 73/23.31, 73/117, 116, 117.2, 117.3

[56] References Cited

U.S. PATENT DOCUMENTS

| | | | |
|---|---|---|---|
| 3,407,646 | 10/1968 | Traver | 73/23.31 |
| 3,603,155 | 9/1971 | Morris et al. | 73/23.31 |
| 3,630,072 | 12/1971 | Traver | 73/23.31 |
| 3,998,095 | 12/1976 | Tinkham et al. | 73/23.31 |
| 4,167,163 | 9/1979 | Moder | 73/23.31 |
| 5,343,906 | 9/1994 | Tibbals, III | 73/23.31 |
| 5,419,178 | 5/1995 | Decker et al. | 73/23.31 |
| 5,431,042 | 7/1995 | Lambert et al. | 73/117.3 |

*Primary Examiner*—Richard Chilcot
*Assistant Examiner*—George M. Dombroske
*Attorney, Agent, or Firm*—Schweitzer Cornman & Gross

[57] ABSTRACT

A method and apparatus for improving the integrity of a vehicle test procedure insures that the vehicle to which a varying test parameter is applied is the same as the vehicle whose response is required. A random variation to the test parameter is introduced, and the response of a chosen vehicle characteristic to the variation is monitored and correlated with the variations. A high correlation confirms that the vehicle whose response is being monitored is in fact the vehicle to which the parameter is applied. The method may advantageously be used in connection with EPA-sanctioned exhaust emission test protocols.

7 Claims, 3 Drawing Sheets

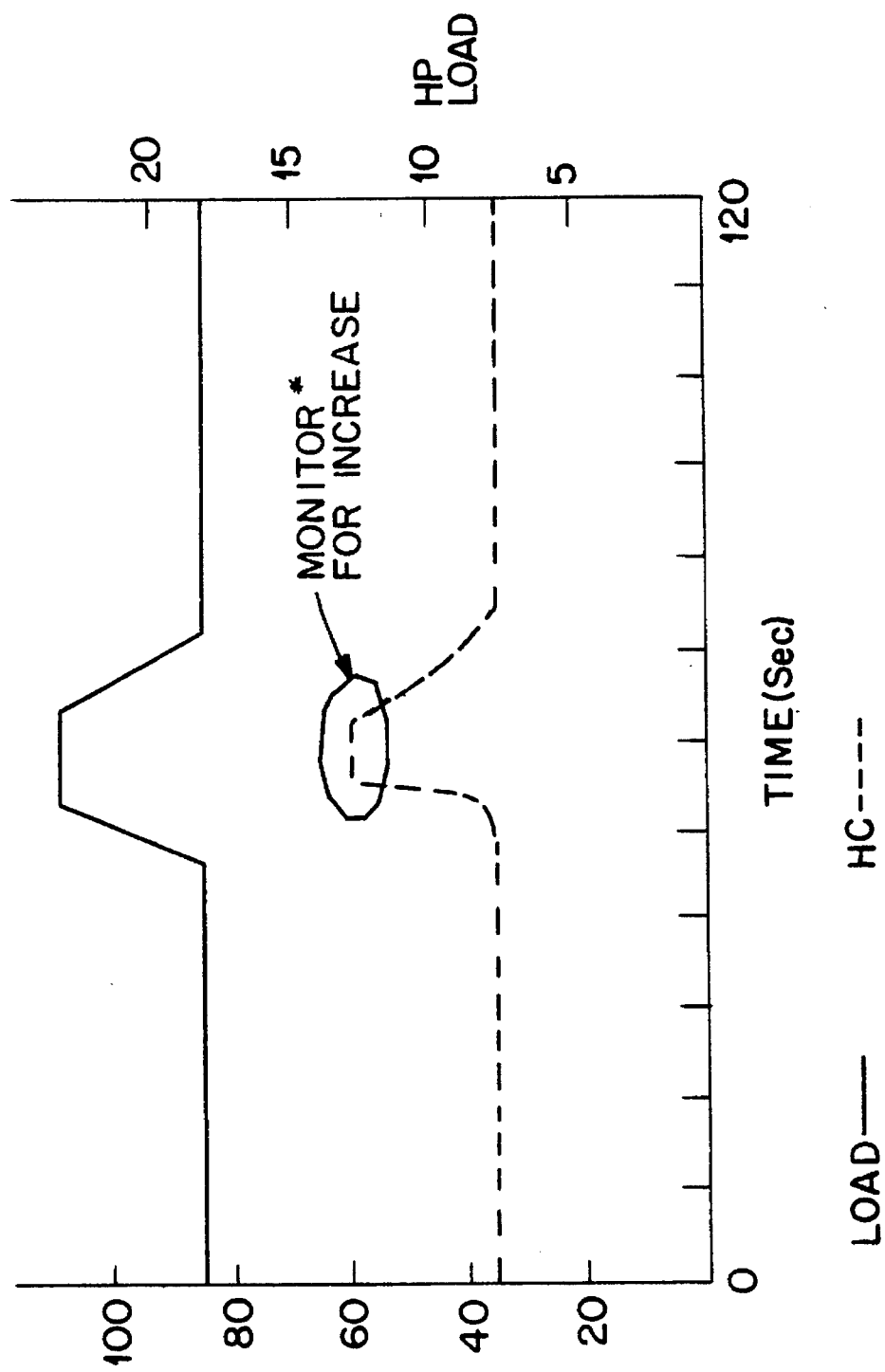

2

METHOD AND APPARATUS FOR INSURING THE INTEGRITY OF VEHICLE TESTING PROCEDURES

BACKGROUND OF THE INVENTION

Exhaust emissions generated by motor vehicles are well recognized and acknowledged as a significant source of airborne pollutants. In efforts to control and reduce such pollutants, programs and standards have been implemented, both on the national and local levels, requiring periodic vehicle monitoring and testing to insure that emissions of the vehicle meet appropriate guidelines.

Industry response to the requirement for testing has been along two parallel paths. Both centralized and de-centralized testing networks have been proposed and implemented. A centralized testing approach provides a minimal number of test locations. While such a system can provide a high degree of security and confidence with respect to the testing procedure, it suffers from a perceived lack of convenience for the consumer, with a limited number of test facilities generating long waiting times.

The alternative path, the decentralized network approach, while more acceptable from the consumer's point of view in that it allows a large number of test facilities to be implemented, has so far been of limited acceptance by the U.S. Environmental Protection Agency (EPA). Under EPA regulations, the degree of compliance of a region with various federal standards is rated by the issuance of "credits" which determine the level of federal funding available to a state for environmental-related projects. As a result of the conclusion by the EPA that tests performed in a decentralized or distributed testing system are subject to inaccuracy, if not fraud, the credits available to a state or region for the implementation of a distributed testing network is typically one-half those available for a centralized testing system. Because of this bias, states have been reluctant to commit to decentralized systems, preferring a centralized approach even if it results in consumer dissatisfaction.

It is thus a purpose of the present invention to provide an emissions system testing methodology and apparatus which provides for an increased level of assurance of the integrity of a vehicle testing procedure.

A further purpose of the present invention is to provide such a methodology which can be applied to a distributed or decentralized testing network approach.

Yet another purpose of the present invention is to provide a testing methodology which can be implemented in testing systems and protocols of conventional structure, without significant cost or inconvenience to either the test system operator or the consumer.

BRIEF DESCRIPTION OF THE INVENTION

In accordance with the above and other objects and purposes, the present invention utilizes a conventional emissions testing system and applied protocol in which a computer-driven analyzer records emissions generated by a vehicle while controlling a dynamometer upon which the vehicle is placed to simulate varying speed and load conditions. By introducing a randomly chosen variation in an applied test parameter, which variation can be associated with a resulting change in a performance parameter for the vehicle, such as the concentration of one of the exhaust components analyzed by the testing apparatus, each individual test protocol performed may be given its own specific signature, which can be located and identified on the analyzer's output. Unless the measured test results include a correlation with the variation applied, an invalid test flag is generated, requiring retest or other appropriate control measures to be taken.

BRIEF DESCRIPTION OF THE DRAWINGS

A fuller understanding of the present invention, and the advantages and objects thereof, will be obtained upon consideration of the following detailed description of the invention when reviewed in association with the annexed drawings, wherein:

FIG. 3 is a similar plot of a portion of a test protocol modified to incorporate a random variation in engine load in accordance with the present invention.

DETAILED DESCRIPTION OF THE INVENTION

Current and proposed enhanced vehicle emission monitoring programs utilize testing modes in which the vehicle under test is subject to a variety of load conditions while its exhaust emissions, measured by a probe inserted into the tailpipe, are recorded for comparison to appropriate standards. A vehicle identifier, such as its Vehicle Identification Number (VIN) or registration number, is entered by keyboard into the testing system to associate the test protocol with the vehicle. Because passage of an emissions test is typically required for re-registration of a vehicle for use, and the cost of repair is often high, there is an incentive for unscrupulous test operators to falsify test results, either by passing a failed vehicle, to the "benefit" of the vehicle's owner, or to fail a passing vehicle to generate repair revenue.

A typical procedure for defeating such a testing protocol is accomplished by performing the test on a vehicle whose test results are known, while entering identification data relating to the vehicle which should be tested. The emissions monitoring printout thus identifies the latter vehicle as being tested when, in fact, it was not under test.

A proposed method of combating such fraudulent testing is to incorporate a camera system to form a video record of the testing process. While this approach can insure that the correct vehicle is positioned on the test lane dynamometer, it can be defeated by inserting the sample probe actually connected to the analyzer in a different vehicle located away from, or out of view of, the recording camera angle, which is typically fixed.

Figure 1:
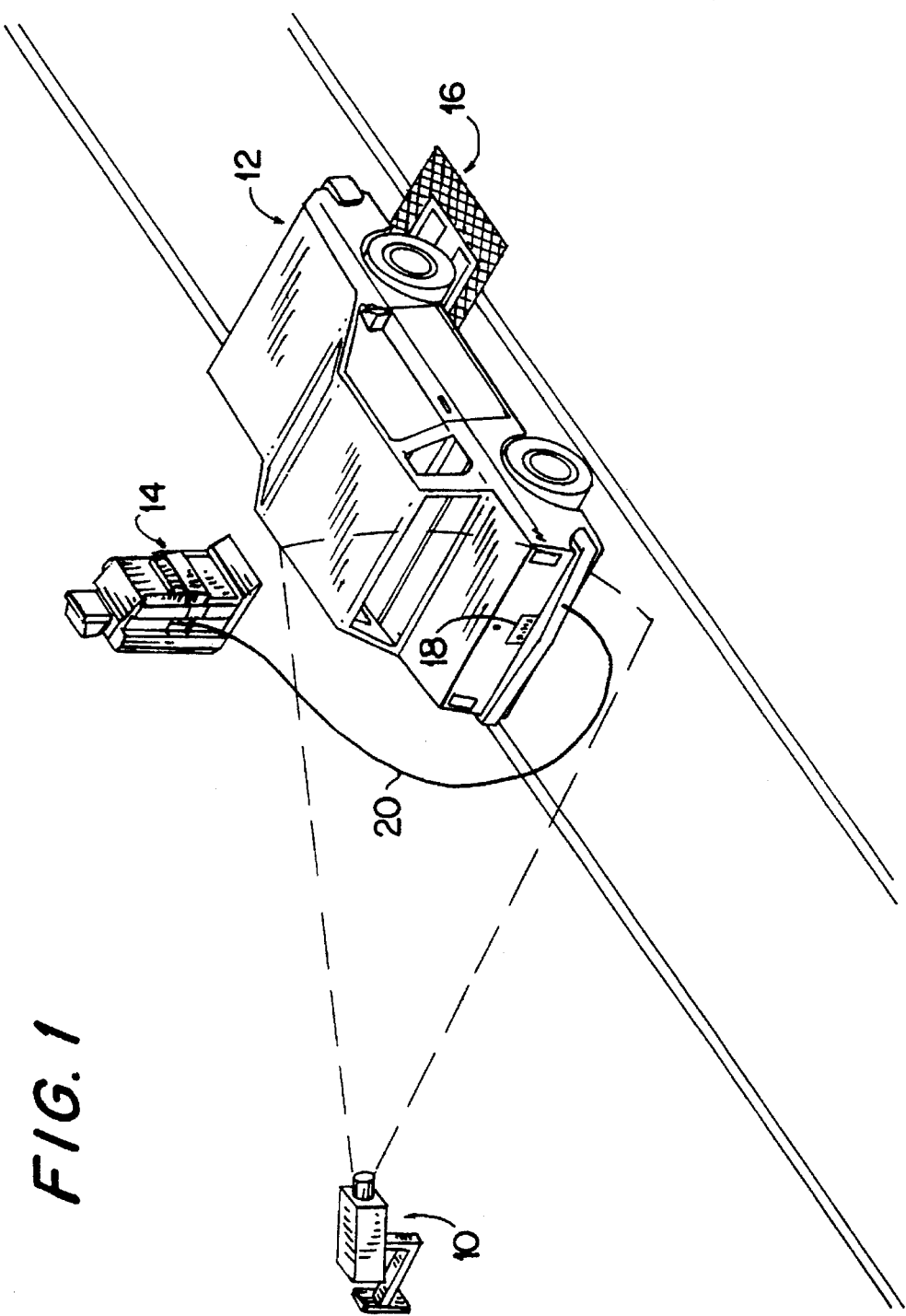
FIG. 1 is a representation of a vehicle emissions test facility with which the present invention is employed.

The present invention eliminates the drawback of a video system by providing an individual signature to the testing process, which signature is not under the control of the test technician. In particular, and as depicted in the FIG. 1, a conventional video surveillance system uses a video camera 10 mounted to observe the rear portion of a vehicle 12 connected to a test apparatus 14 and located upon dynamometer 16. The video camera is oriented such that the license plate 18 of the vehicle is observed to provide identification thereof. The exhaust pipe of the vehicle is connected to the test apparatus analyzer by a probe line 20 which collects the exhaust gases for analysis. As may be appreciated, the probe line and analyzer are not normally within the view of the camera, and thus the camera will provide no assurance that the exhaust of the vehicle under test is actually being received and analyzed by the test equipment.

Figure 2:
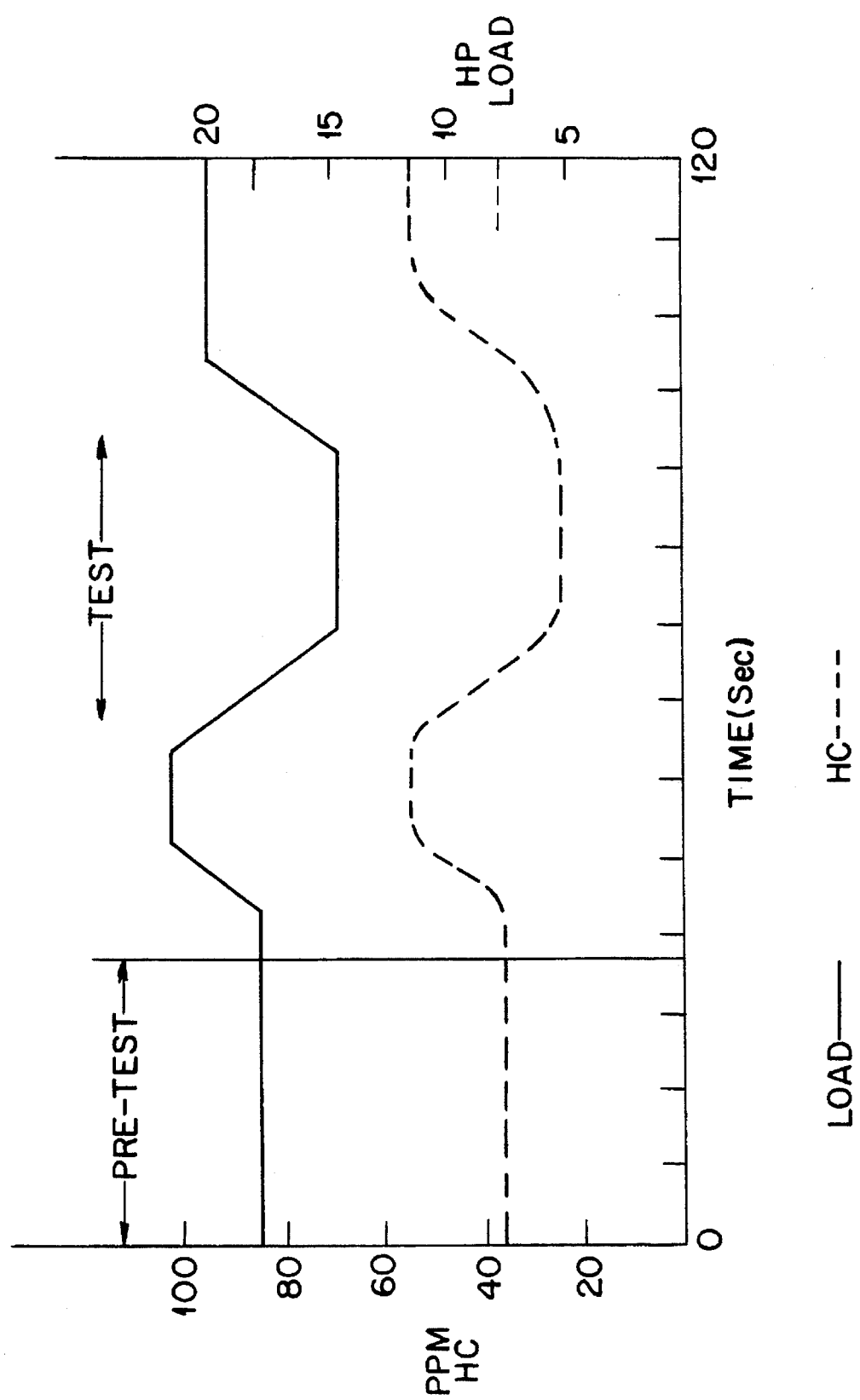
FIG. 2 is a representation of a plot of exhaust hydrocarbon concentration and applied engine load during an emissions test.

As shown in FIG. 2, a typical test protocol will include the monitoring of exhaust constituents, such as total hydrocarbon (HC) level, as the vehicle is subjected to varying operating conditions, simulated by placing a varying load upon the vehicle and engine by the dynamometer 16. After an initial pre-test period during which the system stabilizes, the load is varied in accordance with a predetermined and defined program stored in the microprocessor controller of the analyzer system. It can be appreciated from the plot of FIG. 2, which shows both applied load and exhaust HC concentration, that there is a general relation between load and HC concentration. Similar relationships may be found with respect to load and other constituents, as well as between load and other measurable operating parameters, such as EGR throttle position or other indications sensed or detected by the vehicle's control computer.

The present invention utilizes such a general relationship to apply a unique signature or fingerprint to each test. The microprocessor of test apparatus 14 is programmed as known in the art to include a random variation during the test process. Preferably, such variation is programmed to occur during the pretest portion. As shown in FIG. 3, this variation may be in the form of an increased or decreased load portion. The response of the vehicle under test to the variation is monitored. Since the general relationship between the constituent monitored and load is known, it is a relatively simple task to develop an algorithm to determine if in fact a correlated change in concentration occurs. Appropriate analysis of the magnitude and/or duration of the variation may be used to make the determination.

If the system properly correlates a variation in concentration with the applied load variation, it can be assumed that the vehicle to which the load variation is applied and the vehicle who's output is monitored are in fact one and the same, and the test protocol may continue in a normal manner. If, on the other hand, a correlation is not found, indicating that the vehicle who's exhaust is being monitored is not the same as the vehicle to which the load variation was applied, the system can be programmed to abort the test, ask for a restart, or perform the test protocol with an appropriate warning message being generated. The fact of noncorrelation may also be stored in system memory, and/or can be forwarded by telephone or other communication system to a central facility as may be required.

Since the load variation is generated in a random manner, and is not subject to the control of the system operator, it is impossible for the operator to predict the onset, magnitude or duration of the variation. A "proper" response in the exhaust constituent thus cannot be predicted, preventing the substitution of another vehicle's exhaust output for the exhaust of the vehicle actually under test and placed on the dynamometer.

I claim:

1. A method for improving the integrity of a vehicle emissions test performed on a test apparatus having means for applying a varying test parameter to a vehicle under test and means for collecting an exhaust sample and determining the concentration of an exhaust constituent in response thereto, by determining if said test parameter applying means and said collecting means are associated with the same vehicle, comprising the steps of:

applying a random variation to the test parameter during a test;

monitoring a selected exhaust constituent for a change in concentration associated with said variation;

comparing said change to a standard representing a high level of correlation; and determining whether the degree of similarity between said change and said standard indicate that the variation was applied to the same vehicle whose exhaust constituent was monitored.

2. The method of claim 1, wherein said varying test parameter is dynamometer engine load.

3. The method of claim 2 wherein said exhaust constituent is hydrocarbon concentration.

4. The method of claim 1 wherein the test comprises pre-test and test portions, wherein said random variation is applied during said pre-test portion.

5. A method for improving the integrity of a vehicle test protocol performed on a test apparatus having means for applying a varying test parameter to a vehicle under test and means for monitoring vehicle performance characteristic in response thereto, by determining if said test parameter applying means and said monitoring means are associated with the same vehicle, comprising the steps of:

applying a random variation to the test parameter during a test;

monitoring the performance characteristic for a change associated with said variation;

comparing said change to a standard representing a high level of correlation; and determining whether the degree of similarity between said change and said standard indicates that the variation was applied to the same vehicle whose characteristic was monitored.

6. An apparatus for improving the integrity of a vehicle test protocol performed on a test apparatus having means for applying a varying test parameter to a vehicle under test and means for monitoring a vehicle performance characteristic in response thereto; comprising:

means for applying a random variation to the test parameter during a test;

means for monitoring the vehicle performance characteristic for a change associated with said variation;

means for comparing said change to a standard representing a high level of correlation; and means for determining whether the degree of similarity between said change and said standard indicates that the variation was applied to the same vehicle whose characteristic was monitored.

7. The apparatus of claim 6, wherein said vehicle performance characteristic is the concentration of an exhaust constituent.

* * * * *